(12) United States Patent
Harris et al.

(10) Patent No.: US 8,309,758 B2
(45) Date of Patent: Nov. 13, 2012

(54) ALLYL ACETATE PURIFICATION

(75) Inventors: Stephen H. Harris, Kennett Square, PA (US); Shaw-Chan Lin, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 364 days.

(21) Appl. No.: 12/653,677

(22) Filed: Dec. 17, 2009

(65) Prior Publication Data

US 2011/0152568 A1 Jun. 23, 2011

(51) Int. Cl.
*C07C 67/54* (2006.01)
*C07C 27/02* (2006.01)

(52) U.S. Cl. ........................................ 560/248; 568/877

(58) Field of Classification Search ........................ None
See application file for complete search history.

(56) References Cited

U.S. PATENT DOCUMENTS

| | | | |
|---|---|---|---|
| 3,917,676 A | 11/1975 | Kisaki et al. | |
| 3,925,452 A | 12/1975 | Swodenk et al. | |
| 3,970,713 A | 7/1976 | Scharfe et al. | |
| 4,571,431 A | 2/1986 | Drake | |
| 4,647,690 A | 3/1987 | Drake | |
| 5,011,980 A | 4/1991 | Sano et al. | |
| 5,326,923 A | 7/1994 | Cooper et al. | |
| 7,265,243 B2 | 9/2007 | Chen et al. | |
| 7,344,635 B2 | 3/2008 | Briot et al. | |
| 2006/0084829 A1 | 4/2006 | Saihata et al. | |

FOREIGN PATENT DOCUMENTS

| | | | |
|---|---|---|---|
| GB | 1 306 219 | * | 7/1970 |
| JP | 53-071009 | | 6/1978 |
| JP | 61-238745 | | 10/1986 |
| JP | 01-250338 | | 10/1989 |
| JP | H2-96548 | | 4/1990 |

* cited by examiner

*Primary Examiner* — Rosalynd Keys

(57) ABSTRACT

A process for purifying allyl acetate is disclosed. An acetoxylation mixture is distilled at elevated pressure to remove propylene and generate a first bottoms mixture comprising allyl acetate, acetic acid, acrolein, allyl diacetate, and 3-acetoxypropionaldehyde. The first bottoms mixture is flash vaporized, and the resulting vapor is contacted with a solid acidic catalyst under conditions effective to decompose allyl diacetate and 3-acetoxypropionaldehyde. The flashed product, which comprises allyl acetate, acetic acid, and acrolein, is then distilled to remove acrolein and generate a second bottoms mixture comprising allyl acetate and acetic acid. The second bottoms mixture can be used to manufacture allyl alcohol.

18 Claims, No Drawings

ALLYL ACETATE PURIFICATION

FIELD OF THE INVENTION

The invention relates to a process for purifying allyl acetate, which is produced by acetoxylation of propylene.

BACKGROUND OF THE INVENTION

Allyl alcohol is a valuable intermediate for making allyl ester derivatives, allyl monomers, 1,4-butanediol, and polymers such as styrene-allyl alcohol copolymers. Allyl alcohol can be made by isomerizing propylene oxide, but it can also be made by acetoxylation of propylene, followed by hydrolysis of the resulting allyl acetate.

Acetoxylation to produce allyl acetate is performed by reacting propylene, acetic acid, and oxygen in the vapor phase in the presence of a noble metal catalyst, typically palladium. A heated mixture of the reactants is typically contacted with a bed of supported metal catalyst, and products are separated by distillation.

Acetoxylation of propylene is well known, and many references teach ways to use various promoters to improve catalyst lifetime, productivity, or other important outcomes. See, for example, U.S. Pat. Nos. 4,647,690 and 4,571,431, which teach to make allyl acetate by reacting propylene, acetic acid, and oxygen in the presence of palladium, potassium, and bismuth in the presence of an additional rubidium or magnesium promoter. For a few additional examples, see U.S. Pat. Nos. 3,925,452, 3,917,676, 5,011,980, and 7,265,243.

A variety of schemes have been devised for purifying allyl acetate produced via acetoxylation. Usually, allyl acetate is isolated as an overhead stream in a complicated series of steps involving multiple distillations. For example, Matsuoka et al. (Daicel, Japanese Kokai Publ. No. H2-96548) describes a process in which purified allyl acetate is recovered from an acetoxylation reaction mixture using a series of five distillation columns (see FIG. 1), each of which adds considerable expense to the process. According to the reference, the last two columns (labeled 10-10 and 11-11 in the figure) are unnecessary if the allyl acetate product will be converted directly into allyl alcohol. However, that still leaves three distillation columns. In two of the three columns (labeled 5-5 and 8-8), all of the allyl acetate is recovered overhead, which is energy-intensive. Thus, there is a need to recover purified allyl acetate while avoiding the large capital and energy expense of multi-tower distillation schemes that recover all of the allyl acetate overhead.

Ideally, allyl acetate could be used to produce allyl alcohol without the need to recover the allyl acetate as an overhead distillation product. Complicating matters, however, are high-boiling impurities that form during acetoxylation. One such impurity is allyl diacetate, also known as allylidene diacetate or 1,1-diacetoxy-2-propene. It is essentially an acetal derived from the reaction of acrolein and two equivalents of acetic acid. Most references that discuss allyl acetate manufacture by acetoxylation are silent regarding the formation or removal of allyl diacetate. However, ways to remove allyl diacetate is have been discussed (see, e.g., Japanese Publ. Nos. 01-250338 (Daicel), H2-96548 (Daicel, discussed above), 61-238745 (Kuraray), and 53-071009 (Kuraray)). Usually, an allyl diacetate-containing mixture is isolated as a sidedraw from a distillation tower and simply heated to convert it to a mixture of acrolein, acetic acid, and unconverted allyl diacetate.

We discussed issues with some of these earlier processes in our own recent patent application (see copending application Ser. No. 12/322,650, filed Feb. 5, 2009), which describes a process for purifying acetoxylation mixtures that contain allyl diacetate. By contacting an acetoxylation mixture in the vapor phase with a solid acidic catalyst, we effectively decomposed the allyl diacetate to acrolein and removed it from the intermediate stream. This allowed removal of allyl diacetate, normally a "heavy" impurity, as the more volatile reaction product, acrolein. One way to practice the process involves acetoxylation, allyl diacetate decomposition, distillation to remove and recycle unreacted propylene, and distillation to remove acrolein as a light impurity.

Other impurities further complicate schemes that contemplate recovery of purified allyl acetate while avoiding its recovery overhead. As will be discussed further below, we discovered that acrolein—generated from allyl diacetate decomposition or otherwise present—reacts with acetic acid under conditions normally present in the propylene recovery column reboiler to give 3-acetoxypropionaldehyde, a heavy impurity that has not previously been recognized yet is difficult to separate from allyl acetate.

Unfortunately, the heavy impurities (allyl diacetate, 3-acetoxypropionaldehyde) cannot simply be ignored. If they are allowed to pass through to the allyl acetate hydrolysis step, they can react with the ion-exchange resin used to catalyze the hydrolysis, thereby regenerating acrolein. This acrolein can poison the resin, ultimately forcing a reactor shutdown for bed removal and regeneration.

In sum, a better way to purify allyl acetate that is produced by propylene acetoxylation is needed. A preferred process would avoid the capital and yield-loss costs of using multiple distillation columns and would enable recovery of purified allyl acetate as a bottoms product while eliminating high-boiling impurities. An ideal process could be practiced commercially in conjunction with the two-step manufacture of allyl alcohol from propylene via acetoxylation and allyl acetate hydrolysis.

SUMMARY OF THE INVENTION

The invention is a process for purifying allyl acetate. An acetoxylation mixture is distilled at elevated pressure to remove propylene and generate a first bottoms mixture comprising allyl acetate, acetic acid, acrolein, allyl diacetate, and 3-acetoxypropionaldehyde. The first bottoms mixture is flash vaporized, and the resulting vapor is contacted with a solid acidic catalyst under conditions effective to decompose allyl diacetate and 3-acetoxypropionaldehyde. Thereafter, the flashed product, which comprises allyl acetate, acetic acid, and acrolein, is distilled to remove acrolein and generate a second bottoms mixture comprising allyl acetate and acetic acid. The second bottoms mixture can be used to manufacture allyl alcohol.

DETAILED DESCRIPTION OF THE INVENTION

An acetoxylation mixture is the starting material for the allyl acetate purification process of the invention. By "acetoxylation mixture," we mean a mixture comprising allyl acetate, acetic acid, and propylene. Such mixtures are normally obtained when propylene, acetic acid, and oxygen react in the presence of a noble metal catalyst under conditions effective to generate allyl acetate, which is the desired end product, along with a minor proportion of impurities, which typically include acrolein and allyl diacetate. Water and traces of other components are also usually present in the acetoxylation mixture. The exact content of the acetoxylation mixture will depend upon the nature of the particular acetoxylation process, the catalyst choice, equipment, reaction conditions, and other factors. However, a typical acetoxylation mixture contains (wt.%): propylene (20-60%), allyl acetate (5-40%), and acetic acid (10-50%). The acetoxylation mixture may also contain water (1 to 10%), acrolein (0.01 to 2%), and allyl diacetate (0.1 to 10%).

The acetoxylation mixture is most commonly generated by procedures that are already well known, and are described, for example, in U.S. Pat. Nos. 7,265,243; 5,011,980; 4,647,690; 4,571,431; 3,925,452; and 3,917,676, the teachings of which are incorporated herein by reference. As discussed earlier, a noble metal catalyst, preferably palladium, is used, and the catalyst is advantageously combined with other metals or promoters to increase activity, prolong catalyst lifetime, or enhance conversion and selectivity. One suitable acetoxylation mixture for use in the inventive process is produced by reacting propylene, acetic acid, and oxygen in the presence of palladium supported on alumina and promoted with gold and an alkali metal acetate such as potassium acetate or cesium acetate.

In a first step of the inventive process, an acetoxylation mixture is distilled at elevated pressure to remove propylene and generate a "first bottoms mixture." Preferably, the acetoxylation reaction mixture exits the acetoxylation unit at close to the reaction temperature and is compressed prior to entering the distillation unit. Distillation is performed at elevated pressure under conditions effective to remove propylene overhead while keeping other volatile materials in the first bottoms mixture. A high enough pressure to minimize or eliminate the need for refrigeration to collect overhead propylene is preferred. The acetoxylation mixture has already been described.

The first bottoms mixture comprises allyl acetate, acetic acid, acrolein, and allyl diacetate. Typical amounts (wt.%) in the first bottoms mixture: allyl acetate (10-50%); acetic acid (50-90%); acrolein (0.01-2%); and allyl diacetate (0.1-10%). Additionally, the first bottoms mixture includes 3-acetoxypropionaldehyde, an impurity that apparently forms in the reboiler section of the distillation column, but was not until now recognized. The amount of 3-acetoxypropionaldehyde generated is small but significant, typically a few thousand parts per million in the bottoms mixture. The amount is significant because it is usually enough to poison the acidic ion-exchange resin normally used to hydrolyze allyl acetate to produce allyl alcohol.

Distillation of the acetoxylation mixture is performed at elevated pressure. The pressure used in this distillation is sufficient to keep light organics other than propylene from distilling overhead. The pressure is preferably an amount sufficient to avoid the need for refrigeration in collecting the propylene overhead. Preferably, the pressure is greater than 50 psia, more preferably from 100 to 500 psia, and most preferably from 200 to 300 psia. The reboiler temperature in the distillation column is preferably kept within the range of 180° C. to 230° C., more preferably from 190° C. to 210° C. Preferably, propylene is removed at an overhead temperature greater than 10° C., more preferably from 20° C. to 50° C.

In a second step of the process, the first bottoms mixture is flash vaporized. "Flash vaporization" refers to a process in which a liquid mixture, maintained at elevated temperature and pressure, is rapidly depressurized and is thereby transformed completely or nearly so into the vapor phase. The latent heat contained in the first bottoms mixture promotes its rapid vaporization when the pressure on the mixture is reduced or released. The resulting vapor is contacted, preferably immediately, with a solid acidic catalyst under conditions effective to decompose at least a portion of the allyl diacetate and 3-acetoxypropionaldehyde present in the first bottoms mixture to give acetic acid and acrolein.

Thus, the flashed product, which results from contacting the flash vaporized first bottoms mixture with the solid acidic catalyst, comprises allyl acetate, acetic acid, and acrolein. Typical amounts (wt.%) in the flashed product: allyl acetate (10-50%); acetic acid (50-90%); and acrolein (0.01-2%). The flashed product typically also contains water (1-10%). Two high-boiling impurities are effectively converted to a single low-boiling one (acrolein). Allyl diacetate, essentially an acetal, is "decomposed" or converted to one equivalent of acrolein and two equivalents of acetic acid, while 3-acetoxypropionaldehyde provides one equivalent each of acrolein and acetic acid. Acrolein is more volatile than acetic acid or allyl acetate, so it can be removed conveniently in the next step as an overhead distillation cut. Ideally, most or all of the allyl diacetate and 3-acetoxypropionaldehyde present in the acetoxylation mixture is converted to acrolein. Typical conversions for each range from 50% to 100%, generally at least 75%, and more typically from 85% to 99%.

Suitable solid acidic catalysts are acidic enough to convert at least a portion (preferably all) of the allyl diacetate and 3-acetoxypropionaldehyde contained in the first bottoms mixture to acrolein. However, the solid acidic catalyst should promote conversion without also disturbing the desired allyl acetate product. If the solid acidic catalyst is too aggressive, a side reaction can take place in which allyl acetate and acetic acid react to give propylene glycol diacetates; this side reaction is preferably avoided.

Suitable solid acidic catalysts generally include clays; mixed oxides (silica-aluminas, silica-titanias, alumina-borias, silica-zirconias, silica-magnesias, and the like); molecular sieves and zeolites; ion-exchange resins; heteropolyacids; inorganic oxides, sulfates, nitrates, phosphates (e.g., AlPOs and SAPOs), and halides; activated carbons; and the like, and mixtures thereof. Additional suitable solid acidic catalysts are described in U.S. Pat. Nos. 7,344,635 and 5,326,923, the teachings of which are incorporated herein by reference, and in K. Tanabe et al., *New Solid Acids and Bases: Their Catalytic Properties*, Elsevier, New York (1989). Preferred solid acidic catalysts have relatively low acidity. Silica-aluminas and ammonium or metal-containing Y-zeolites, are particularly preferred. Suitable solid acidic catalysts include Davicat® SMR silica-alumina catalysts (product of GraceDavison) and the like. The solid acidic catalyst can be used in any desired form or shape, i.e., powder, granules, tablets, extrudates, or the like.

The flash vaporized first bottoms mixture and the solid acidic catalyst are preferably contacted at or about atmospheric pressure and at a temperature within the range of 60° C. to 200° C., more preferably from 140° C. to 190° C.

After treatment with the solid acidic catalyst, most or all of the flashed product is distilled to remove acrolein, preferably as an overhead cut, and generate a second bottoms mixture comprising allyl acetate and acetic acid. Typical amounts (wt.%) in the second bottoms mixture: allyl acetate (10-50%) and acetic acid (50-90%). The second bottoms mixture usually also contains water and some allyl alcohol. This distillation is preferably performed at or about atmospheric pressure. Preferably, acrolein is removed at an overhead temperature less than 80° C., more preferably from 50° C. to 70° C., most preferably from 55° C. to 65° C. The reboiler temperature in the distillation column is preferably kept within the range of 80° C. to 150° C., more preferably from 100° C. to 130° C. Because this distillation is performed at relatively low temperature, acrolein tends not to react with acetic acid to produce 3-acetoxypropionaldehyde in this column.

The second bottoms mixture is essentially an upgraded allyl acetate stream that has limited value in and of itself. However, it is well-suited for use as a feedstock in a hydrolysis reaction for making allyl alcohol, a compound used to make 1,4-butanediol, pesticides, drugs, and a variety of polymer resins, including CR-39 resin and styrene-allyl alcohol copolymers. Any suitable reagent(s) for hydrolyzing allyl acetate to allyl alcohol can be used. In one preferred approach, the second bottoms mixture is contacted with water and an acidic catalyst, preferably an acidic ion-exchange resin according to well-known methods under conditions effective to convert at least a portion of the allyl acetate to allyl alcohol. The allyl alcohol is then recovered and purified by conventional techniques. Typically, a sulfonic acid resin (such as Amberlyst 15) is used. See, e.g., U.S. Pat. No. 3,970,713, the teachings of which are incorporated herein by reference, Brit. Pat. No. 1,306,219, and U.S. Pat. Appl. Publ. No. 2006/0084829.

The inventive process offers many advantages, including at least one of:

1. Conversion of high-boiling impurities to acrolein. Because allyl diacetate and 3-acetoxypropionaldehyde are converted to acrolein, high-boiling impurities are eliminated in favor of a low-boiling one. This enables purification of allyl acetate by distillation to remove just a small fraction of low-boiling material as an overhead cut. In more conventional purifications, the skilled person distills most or all of the desired allyl acetate to leave the higher-boiling impurities behind in a residue. Such an alternative is energy-intensive, cost-prohibitive, and sacrifices valuable allyl acetate product in the residue.

2. Eliminates impurities that would interfere with allyl acetate hydrolysis. Unless they are eliminated, the high-boiling impurities noted above will carry through to the hydrolysis stage. Although they are typically present at low concentrations, they can still poison ion-exchange resins used as catalysts for hydrolyzing allyl acetate to allyl alcohol. In particular, 3-acetoxypropionaldehyde can regenerate acrolein in the presence of the resin, ultimately fouling it.

3. Efficient energy utilization. Unreacted propylene from acetoxylation mixtures is most conveniently removed by distillation at elevated pressure to leave behind a first bottoms mixture. This takes advantage of the heat used and generated during acetoxylation. The same heat is used in the inventive process to flash vaporize the first bottoms mixture and accelerate conversion of the high-boiling impurities to acrolein. Moreover, removing propylene at high pressures eliminates the need for expensive refrigeration to condense the propylene.

4. Simple to practice. Flash vaporization of the first bottoms mixture and contacting it with a solid acidic catalyst under controlled temperatures and pressures is straightforward. No special reagents or equipment are needed.

5. Easy to integrate. The inventive process can be combined seamlessly with both the acetoxylation and the allyl acetate hydrolysis steps normally practiced.

The following examples merely illustrate the invention. Those skilled in the art will recognize many variations that are within the spirit of the invention and scope of the claims.

COMPARATIVE EXAMPLE 1

Allyl Diacetate Decomposition Precedes Propylene Recovery

Propylene, acetic acid, and oxygen react in the presence of a palladium catalyst to give an acetoxylation mixture comprising (wt.%): propylene (~39%), acetic acid (18%), allyl acetate (12%), water (4.8%), allyl diacetate (0.8%), and acrolein (0.07%); along with propane, argon, and carbon dioxide. The mixture is contacted in the vapor phase with a bed of silica-alumina catalyst at 160° C. to decompose the allyl diacetate, and the acrolein content increases to 0.38 wt.%. Thereafter, the mixture is compressed and sent to a distillation column to recover propylene. After removing propylene at a maximum reboiler temperature of ~190° C. and a pressure of ~200 psia, the concentrated bottoms mixture comprises approximately (wt. %): acetic acid (~50%), allyl acetate (~35%), water (~13%), acrolein (~0.8%), and 3-acetoxypropionaldehyde (~0.4%).

This example shows that following propylene removal, the amount of acrolein remaining in the product mixture is about 1 wt.%, and some acrolein has reacted with acetic acid to generate 3-acetoxypropionaldehyde. Comparative Examples 2 and 3 further explore the reaction of acrolein and acetic acid under conditions that favor propylene removal without excessive refrigeration.

COMPARATIVE EXAMPLE 2

Kinetics of 3-Acetoxypropionaldehyde Formation

A simplified mixture is prepared to simulate the composition of a reaction mixture obtained generally as described in Comparative Example 1. The mixture contains (wt.%): acetic acid (86%), water (13%), and acrolein (1.0%). The mixture is heated in a sealed container at 125° C. for 0.5 h to simulate conditions of a propylene reboiler operating at moderate temperatures and pressures. After 0.5 h, 26% of the acrolein is converted to 3-acetoxypropionaldehyde.

COMPARATIVE EXAMPLE 3

Kinetics of 3-Acetoxypropionaldehyde Formation

A second simplified mixture contains (wt.%): acetic acid (88.9%), water (9.4%), and acrolein (1.7%). The mixture is heated in a sealed container at 190° C. for 0.5 h to simulate conditions of a propylene reboiler operating at somewhat higher temperatures and pressures. After 0.5 h, 18% of the acrolein is converted to 3-acetoxypropionaldehyde.

Comparative Examples 2 and 3 show that acrolein will react in a propylene reboiler operating at elevated pressure and temperature to form substantial levels of 3-acetoxypropionaldehyde. The 3-acetoxypropionaldehyde would not be isolated from the desired allyl acetate product in the next step, which involves removal of acrolein by distillation at atmospheric pressure and milder temperatures. It therefore carries through to the next step, i.e., hydrolysis of allyl acetate in the presence of an acidic ion-exchange resin to give allyl alcohol. Unfortunately, 3-acetoxypropionaldehyde decomposes in the presence of the resin to give acrolein, which can foul the resin and eventually force a unit shutdown.

EXAMPLE 4

Purification of Allyl Acetate

Propylene, acetic acid, and oxygen react in the presence of a palladium catalyst to give an acetoxylation mixture comprising (wt.%): propylene (~39%), acetic acid (18%), allyl acetate (12%), water (4.8%), allyl diacetate (0.8%), and acrolein (0.07%); along with propane, argon, and carbon dioxide. The hot reaction mixture is sent to a propylene recovery distillation column, which is operated at relatively high pressure (200 psia) to enable propylene removal without requiring an expensive refrigeration unit. The temperature at the top of the column is 30° C., and the reboiler temperature is kept at 190° C. Propylene is removed overhead, and a first bottoms stream comprising (wt.%): allyl acetate (26%), acetic acid (40%), acrolein (0.2%), allyl diacetate (1.83%), and 3-acetoxypropionaldehyde (0.15%) is recovered.

The first bottoms stream is fed while hot to a decomposition unit that contains a bed of silica-alumina catalyst. Rapid reduction of pressure causes the stream entering this unit to flash vaporize and contact the silica-alumina catalyst at 140° C. The decomposition unit converts allyl diacetate to acrolein and acetic acid, and converts 3-acetoxypropionaldehyde to acrolein and acetic acid.

The flashed vapor exits the decomposition unit and enters a distillation column, which operates at atmospheric pressure. Acrolein and other lights are removed overhead at a maximum overhead temperature of ~65° C. The remaining second bottoms mixture should comprise allyl acetate (~30%) and acetic acid (~50%). It should contain less than 6 ppm of acrolein, less than 6 ppm of allyl diacetate, and less than 1 ppm of 3-acetoxypropionaldehyde.

EXAMPLE 5

Conversion of 3-Acetoxypropionaldehyde to Acrolein

A reactor tube is filled with 10 cm³ of silica-alumina catalyst (Davicat® SMR catalyst, 14/30 mesh, product of Grace-Davison) and a preheat zone of 10 cm³ of glass beads. The catalyst bed is kept at 140° C. The feed is from an acetoxylation reactor product that is vented to remove propylene and then heated to generate the 3-acetoxypropionaldehyde. Feed composition (wt.%): acetic acid (71%), allyl acetate (16.5%), water (7.2%), allyl diacetate (3.7%), 3-acetoxypropionaldehyde (0.36%), acrolein (0.075%), and some organic lights. Feed rate: 10 g/h. Nitrogen flow: 20 L/h at 80 psig. The final product collected in the liquid phase shows no 3-acetoxypropionaldehyde and 0.19% allyl diacetate.

This example demonstrates that 3-acetoxypropionaldehyde can be successfully converted to acrolein by heating it in the presence of a silica-alumina catalyst.

COMPARATIVE EXAMPLE 6

Attempted Thermolysis of 3-Acetoxypropionaldehyde

The product from Comparative Example 2 is distilled to remove acrolein. The column temperature and reflux rate are controlled to maintain a 2-h residence time for the 3-acetoxypropionaldehyde. However, no measurable amount of 3-acetoxypropionaldehyde is converted to acrolein; the aldehyde impurity is simply concentrated in the allyl acetate product.

The examples are meant only as illustrations. The following claims define the invention.

We claim:

1. A process for purifying allyl acetate, comprising:
   (a) distilling an acetoxylation mixture comprising allyl acetate, acetic acid, and propylene at elevated pressure to remove propylene and generate a first bottoms mixture comprising allyl acetate, acetic acid, acrolein, allyl diacetate, and 3-acetoxypropionaldehyde;
   (b) flash vaporizing the first bottoms mixture and contacting the resulting vapor with a solid acidic catalyst under conditions effective to decompose allyl diacetate and 3-acetoxypropionaldehyde and provide a flashed product comprising allyl acetate, acetic acid, and acrolein; and
   (c) distilling the flashed product to remove acrolein and generate a second bottoms mixture comprising allyl acetate and acetic acid.

2. The process of claim 1 wherein propylene is removed at a pressure greater than 50 psia and at an overhead temperature greater than 10° C.

3. The process of claim 1 wherein the catalyst is selected from the group consisting of clays; mixed oxides; molecular sieves and zeolites; ion-exchange resins; heteropolyacids; inorganic oxides, sulfates, nitrates, phosphates, and halides; activated carbons; and mixtures thereof.

4. The process of claim 1 wherein steps (b) and (c) are performed at or about atmospheric pressure.

5. The process of claim 1 wherein the vapor and the solid acidic catalyst are contacted in step (b) at a temperature within the range of 60° C. to 200° C.

6. The process of claim 1 wherein acrolein is removed in step (c) at a maximum overhead temperature within the range of 50° C. to 70° C.

7. The process of claim 1 wherein the second bottoms mixture is hydrolyzed to produce allyl alcohol.

8. The process of claim 7 wherein the hydrolysis is accomplished by contacting the second bottoms mixture with an acidic ion-exchange resin.

9. The process of claim 1 wherein, in (b), the flash vaporized first bottoms mixture is contacted with the solid acidic catalyst at or about atmospheric pressure and at a temperature of from 140° C. to 190° C.

10. The process of claim 1 wherein the flashed product provided in (b) comprises about 10-50 wt. % allyl acetate, about 50-90 wt. % acetic acid, and about 0.01-2 wt. % acrolein.

11. The process of claim 1 wherein the flashed product generated in (c) comprises about 10-50 wt. % allyl acetate, and about 50-90 wt. % acetic acid.

12. A process for purifying allyl acetate, comprising:
   (a) distilling an acetoxylation mixture comprising allyl acetate, acetic acid, and propylene at elevated pressure to remove propylene and generate a first bottoms mixture comprising allyl acetate, acetic acid, acrolein, allyl diacetate, and 3-acetoxypropionaldehyde;
   (b) flash vaporizing the first bottoms mixture and contacting the resulting vapor with a solid acidic catalyst under conditions effective to decompose allyl diacetate and 3-acetoxypropionaldehyde and provide a flashed product comprising allyl acetate, acetic acid, and acrolein; and
   (c) distilling the flashed product to remove acrolein and generate a second bottoms mixture comprising allyl acetate and acetic acid,
   wherein propylene is removed at a pressure within the range of 100 to 500 psia, a reboiler temperature within the range of 180° C. to 230° C., and an overhead temperature within the range of 20° C. to 50° C.

13. The process of claim 12 wherein the catalyst is selected from the group consisting of clays; mixed oxides; molecular sieves and zeolites; ion-exchange resins; heteropolyacids; inorganic oxides, sulfates, nitrates, phosphates, and halides; activated carbons; and mixtures thereof.

14. The process of claim 12 wherein steps (b) and (c) are performed at or about atmospheric pressure.

15. The process of claim 12 wherein the vapor and the solid acidic catalyst are contacted in step (b) at a temperature within the range of 60° C. to 200° C.

16. The process of claim 12 wherein acrolein is removed in step (c) at a maximum overhead temperature within the range of 50° C. to 70° C.

17. The process of claim 12 wherein the second bottoms mixture is hydrolyzed to produce allyl alcohol.

18. The process of claim 17 wherein the hydrolysis is accomplished by contacting the second bottoms mixture with an acidic ion-exchange resin.

\* \* \* \* \*